United States Patent [19]

Contant

[11] 4,057,852
[45] Nov. 15, 1977

[54] ANTI-DAZZLE EYE SHADE

[76] Inventor: Claude Contant, 232 Boulevard de la Madeleine, Nice, France, 06000

[21] Appl. No.: 659,135

[22] Filed: Feb. 18, 1976

[30] Foreign Application Priority Data

Feb. 18, 1975 France .................. 75.05892

[51] Int. Cl.² .................................... A61F 9/00
[52] U.S. Cl. ............................................... 2/12
[58] Field of Search .............. 2/12, 13, 14 R, 14 E, 2/14 F, 14 J, 14 M; 351/44, 45

[56] References Cited

U.S. PATENT DOCUMENTS

| 865,484 | 9/1907 | Ellis | 2/12 |
|---|---|---|---|
| 2,187,810 | 1/1940 | Rentz | 2/12 X |
| 2,342,377 | 2/1944 | Small | 2/12 |
| 2,999,426 | 9/1961 | Hanke | 2/12 X |
| 3,092,838 | 6/1963 | Vacha | 2/12 |

FOREIGN PATENT DOCUMENTS

| 69,197 | 7/1951 | Netherlands | 2/14 J |
|---|---|---|---|
| 305,513 | 2/1929 | United Kingdom | 2/12 |

Primary Examiner—Werner H. Schroeder
Assistant Examiner—Peter Nerbun
Attorney, Agent, or Firm—Browdy and Neimark

[57] ABSTRACT

An anti-dazzle eye shade for protection against natural or artificial light rays in a reliable and effective safety system for protection of drivers against dazzling. An opaque or slightly transparent support is adapted to be held to the wearer's head at the level of the eyes. The support has an upper horizontal part, a front vertical part and two side blinders. The front part has sloped cutouts at the level of the eyes and is provided with laterally slidable portions each having a notch flared toward the bottom. The notched portions may be adjusted to the visual field of the wearer. In this way maximum protection of the eyes is obtained against all radiation outside of the direct field of vision of the wearer.

8 Claims, 8 Drawing Figures

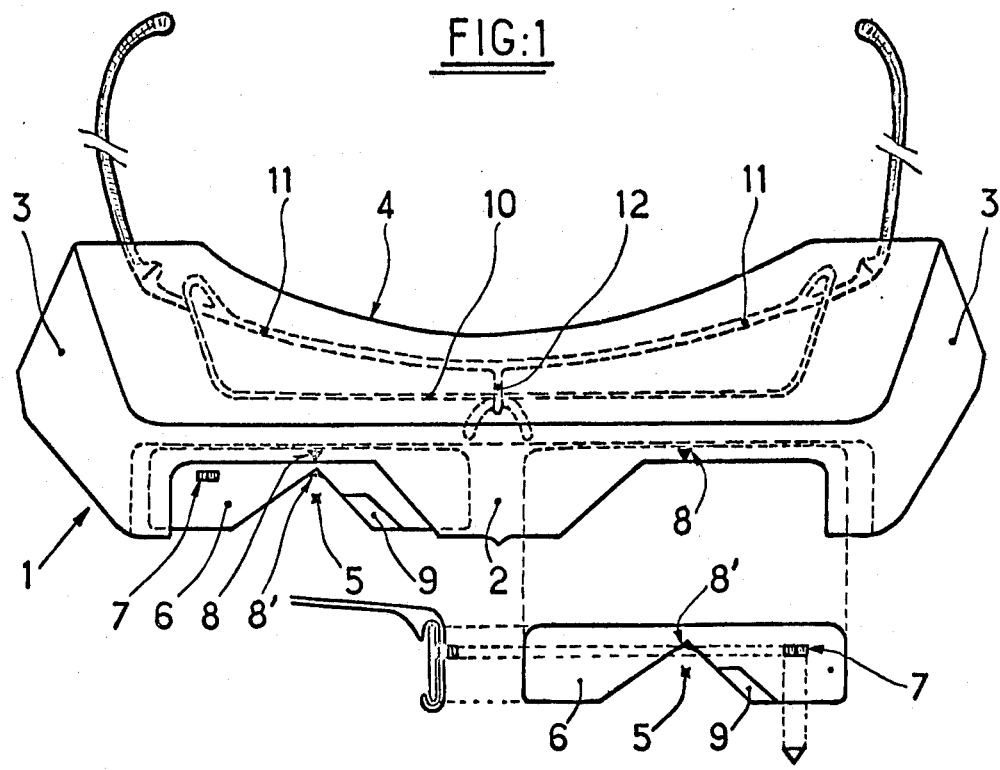
FIG:1
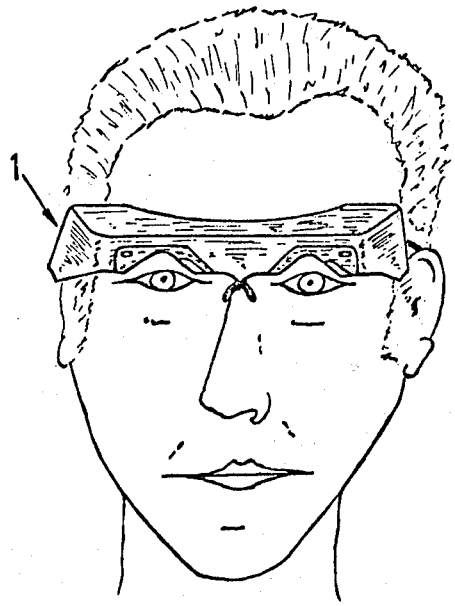
FIG:2
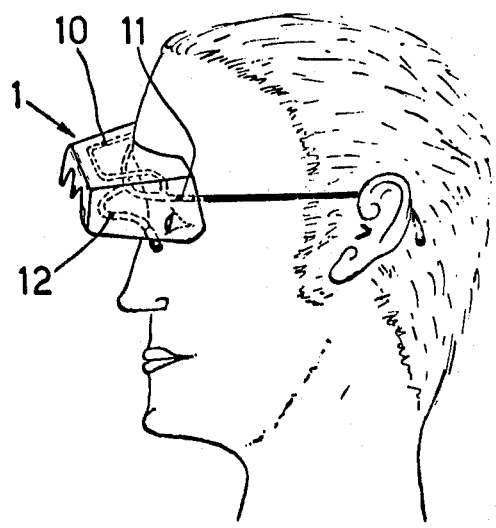
FIG:3

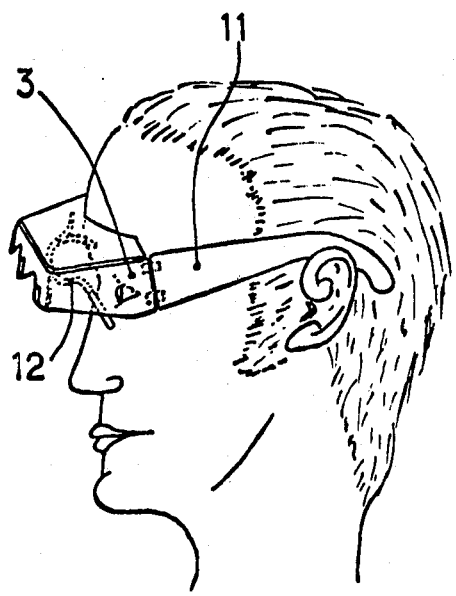
FIG:4
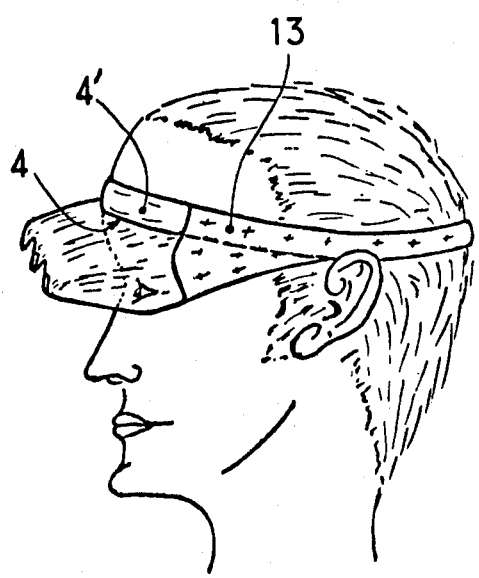
FIG:5
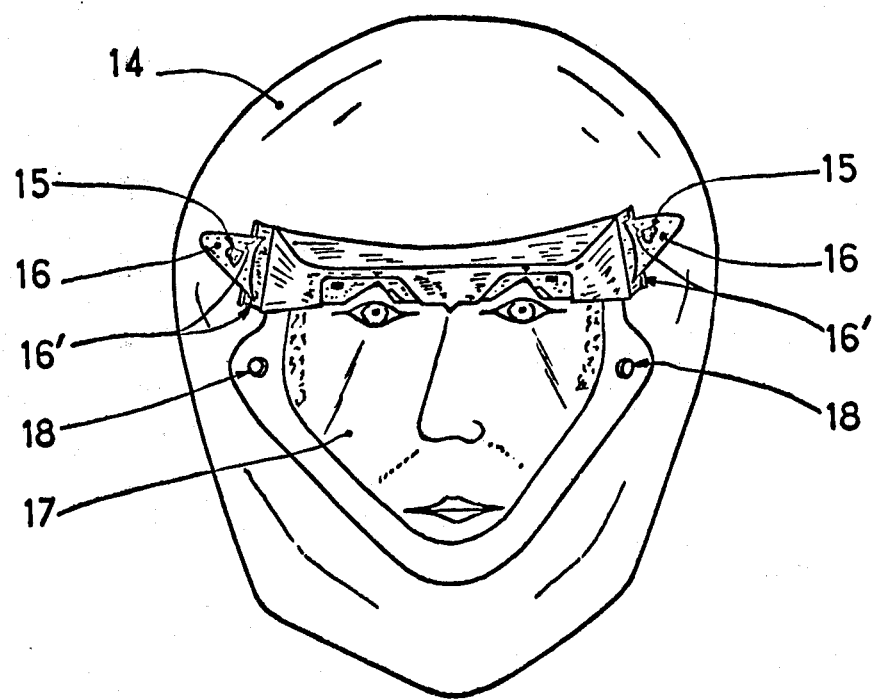
FIG:6

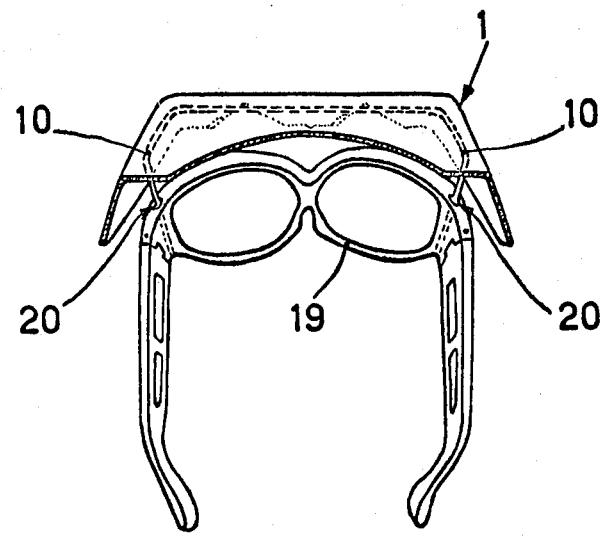
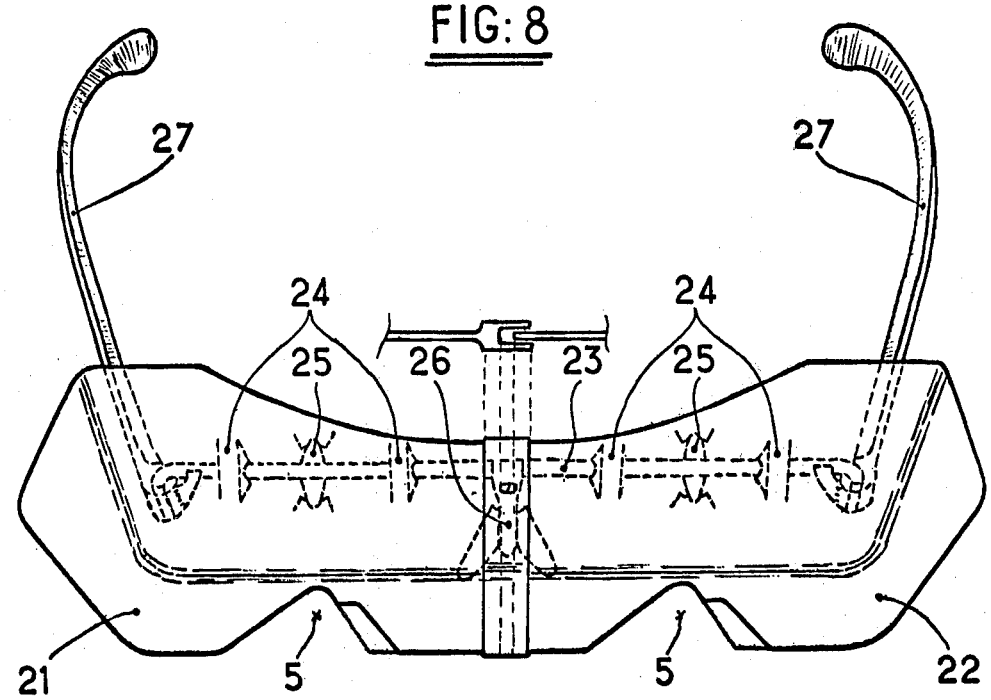

ANTI-DAZZLE EYE SHADE

FIELD OF THE INVENTION

The present invention relates to the area of devices for protecting drivers of vehicles against sudden difficulties with vision, caused by natural or artificial light rays. More specifically, it concerns a new device called an anti-dazzle visor which allows elimination of eye fatigue and preservation of perfect vision when facing disturbing light rays.

BACKGROUND OF THE INVENTION

It is well known that the dazzling of drivers of vehicles, either in the daytime by the sun or especially at night by oncoming headlights, creates actual temporary blindness and is the cause of numerous and serious traffic accidents.

In order to attempt to overcome these disadvantages, various systems have been proposed, either built into the vehicle itself (movable sun visors, tinted windshields, adjustable rearview mirrors) or designed for the driver (sun glasses, special night glasses, filter lenses). Unfortunately, these systems are not very effective. For example, the sun visor system, or the classic visor, only protects the eyes in a horizontal plane; as a result, when the sun is very low on the horizon or when the headlights of a vehicle coming in the opposite direction are dazzling, these systems cannot protect the driver's eyes without obstructing his view of the road. In addition, the mobility of sun visors is not always satisfactory and the curvature and contour of the highway requires difficult and dangerous maneuvers which do not eliminate the sudden dazzle which often happens when rounding a corner. Tinted windshields or special glasses, besides their additional cost (high cost), have the disadvantages of being poorly adaptable to the user, and cannot be adjusted as a function of brightness, and in many instances themselves constitute additional causes of danger by a permanent reduction of the field of vision or of brightness.

SUMMARY OF THE INVENTION

The goal of the present invention is to solve the problem of developing an anti-dazzle system which does not have the disadvantages listed above and protects vision at all times against all manner of light rays, including those transmitted by the rearview mirror, regardless of the position of their source relative to the driver without his view of the road being obscured. For this purpose, a technical solution is proposed in which no artificial shield is interposed between the driver's eye and the light ray and in which, however, maximum protection of the eyes is obtained against all radiation outside the direct field of vision of the driver.

The device which is the object of the invention constitutes a genuine safety system, reliable and effective against dazzling of all drivers. It has an enormous field of application for driving, as well as piloting of various land, marine and air vehicles, as well as other activities, especially sports.

The new anti-dazzle eye shade or visor according to the present invention is essentially characterized by the fact that it is composed of a support with the following: a horizontal part with a curved side which can be adapted to the wearer's head and an essentially vertical front part, these two parts being joined together at the side to form blinders at the level of the temples, the front part being provided at the level of the wearer's eyes with sloping cutouts, in each of which a part with a notch which is flared toward the bottom is free to slide laterally, allowing selective adjustment of the visual field of the wearer; this visor is also provided with means of adaptation for the wearer.

According to a particularly advantageous characteristic of the present invention, the notched parts are provided with pushbuttons and marks corresponding to other marks on the visor so that the visual fields of the two eyes can be made to coincide and to effect adjustment that provides a clear view beneath the notches. In addition, one part of one of the sides of the notched part is made of tinted transparent material to absorb or reduce the intensity of the light rays reaching the eye at a certain angle.

In practice, the visor can be made in one piece from flexible material (for example, plastic or the like), reinforced by an armature made of deformable metal wire in order to allow it to be bent inward more or less to adapt to the shape of the user's face. In one version, the visor can be made in two symmetrical halves, right and left, assembled with tight friction along a median axis, so as to allow lateral displacement and inclination of said halves around this axis, allowing the visor to be adjusted and positioned by the wearer at will.

According to another characteristic of the present invention, the means for adaptation of the visor to the wearer may be of several types. According to one embodiment, the front surface of the visor is fixed, by means of an armature made of deformable metal wire, to a frame of the eyeglass type which is adaptable to the wearer's ears. In addition, the frame is advantageously provided with an adjustable central nose piece intended to rest securely on the wearer's nose. In one embodiment, the sides rest on the ears and are hinged directly to the sides of the visor, and the fixed central nose piece is beneath the visor. In another version of the embodiment, the visor is adapted for clipping to a pair of eyeglasses, for example by forcing the ends of said armature into holes or small tubes soldered on the eyglass frame. Accordingly to a modification the eyeglass-type frame and its central nose piece are replaced by a simple elastic band or equivalent means; the latter allows a more convenient adaptation to the head by a wearer who must wear corrective lenses, and for sports, and also allows the visor to be mounted on a motorcycle helmet, with or without a face shield. According to still another version, the visor is designed to be mounted on a motorcycle helmet by means of two knurled screws, and with two straps, allowing it to be positioned at the desired level on the helmet, parallel to the two eyes.

BRIEF DESCRIPTION OF THE DRAWINGS

The invention will be better understood from the detailed description of various embodiments, cited for the sake of illustration, with reference to the accompanying drawings, in which:

FIG. 1 shows a view of all of the component elements of the new visor, according to a preferred embodiment.

FIGS. 2 and 3 show a front elevation and a side elevation, respectively, of the installation of the visor at the level of the eyes and nose of the wearer.

FIG. 4 is a variation in the manner of attachment of the visor to the wearer's head.

FIG. 5 is another variation in the manner of attachment of the visor to the wearer's head.

FIG. 6 shows the adaptation of the system to a motorcycle helmet.

FIG. 7 shows a fixed non-limiting manner of attachment for the visor on a pair of corrective eyeglasses or sun glasses.

FIG. 8 shows a view of all the component elements of the visor according to another embodiment.

DETAILED DESCRIPTION OF PREFERRED EMBODIMENTS

The visor shown in FIG. 1 and corresponding to general reference 1 involves a front element 2 which is essentially vertical and is extended along the sides in the form of two blinders 3 as well as a cutout in the front part 4 with a rounded shape which facilitates contact with the wearer's forehead. The front surface is provided at the level of the wearer's eyes with two parts 6 having a notch 5 widened toward the bottom and with an appropriate shape, intended to allow the driver to continue seeing the road when he is obliged to tilt his head downward a considerable distance in order to protect himself against the light rays which are dazzling him. Parts 6 can slide laterally without producing a gap either at the top or sides, thus allowing notches 5 to be set at the same spacing as the wearer's eyes, allowing a clear view and simultaneous protection of both eyes. The wearer can easily shift parts 6 by operating pushbuttons 7. Marks 8 and 8', provided respectively above notch 5 on parts 6 and on the front surface of the visor, allow determination in an accurate manner of whether the notches are centered or displaced toward the right or left, to set the preferred position, and also to reposition parts 6 more easily after accidental displacement or use of the visor by a third person. In addition, it is interesting to make one part 9 of part 6, on the right or left depending on the side of the road used by the drivers in a given area, made of tinted material, preferably red, so that the driver can, by tilting his head downward, recover his vision without losing sight of the on-coming vehicles and without being dazzled by the bright light rays at the level of his eyes when he turns his head in their direction.

According to a version of the embodiment shown in FIG. 8, the visor can be made in two symmetrical parts which overlap slightly, a right 21 and left 22, assembled with firm friction by means of bearings 24 and flat springs 25, along a median axis 23 provided at the center with an adjustable nose piece 26 designed to rest on the wearer's nose, and two parts 27 which pivot at their ends, intended to rest on the wearer's ears. The two parts 21 and 22 can be shifted laterally and tilted around axis 23 in order to allow the wearer to adjust the notches 5 to the spacing of his eyes, to raise and lower the visor at will.

In practice, the visor is advantageously made of a light material as for example cast or injection molded plastic, opaque or slightly transparent, and with convenient thickness.

The attachment of the first embodiment of the device to the wearer's head can be accomplished in several ways. According to the methods illustrated in FIGS. 1 to 3, the visor 1 is attached, for example by means of a deformable metal wire armature 10 allowing precise and stable adjustment in the horizontal and vertical planes, to a frame 11 of the eyeglass type which allows precise, easy, and rapid attachment of the system to the wearer's forehead. In addition, frame 11 is provided with a central nose piece 12 which is adjustable in all directions, and is intended to rest properly on the wearer's nose and to allow the visor to be positioned at the desired height on the forehead. In another embodiment which is shown in FIG. 4, sides 11 are articulated directly to blinders 3 and adjustable nose piece 12 is similarly attached to the upper part of the visor. In another embodiment, shown in FIG. 5, frame 11 and central nose piece 12 are replaced by a simple elastic ribbon 13 attached by any known means to part 4', added to the front part 4 of visor 1. This simpler embodiment, with reduced cost, allows superposition on corrective eyeglasses permanently worn by a wearer, but it of course involves an obligation to find the suitable position for each use.

FIG. 6 shows a method of adaptation of a visor according to the invention to a motorcycle helmet 14. In this case the visor is attached on both sides by means of knurled screws 15 which, by means of straps 16 fitted with clips 16', hold the visor on the helmet; this attachment allows precise adjustment in the horizontal and vertical planes and also does away with the need for replacing the visor accurately on the helmet, thanks to the marks left by clips 16' on the sides of the visor. When the helmet is provided with a face shield 17, snaps 18 can be provided to facilitate the attachment and removal of this protective shield.

In FIG. 7, there is a schematic diagram of a manner of attachment 1 according to the invention for a pair of eyeglasses 19 in the case where the wearer is required to use such corrective elements at all times or when he desires to wear the visor and sun glasses simultaneously; in the latter case, the eyeglasses may be fitted with filtering lenses which are tinted and vary with brightness, of the "Variflux" or "Photosun" type, all with removable lenses or with any other means for use of this assembly at night. The two ends of armature 10 on the visor are then fitted into two holes 20 provided in the eyeglass frame or in small tubes soldered to the frame.

Of course, other embodiments, and adaptations may be provided without going beyond the scope of the invention, for the notched visor with elements for adjusting the visual field.

It will be obvious to those skilled in the art that various changes may be made without departing from the scope of the invention and the invention is not to be considered limited to what is described in the specification.

What is claimed is:

1. An anti-dazzle visor to selectively limit the wearer's unobstructed field of view for protection against natural or artificial light rays from outside said limited field of view, comprising a support and adaptation means for adapting said support to the wearer, said support comprising:

a horizontal part with a curved side for adjustment to the wearer's head;

an essentially vertical front part connected at the top thereof to said horizontal part at the side thereof opposite said curved side, said front part being provided at the level of the wearer's eyes with sloping cutouts, said cutouts being held at a distance in front of the eyes determined by the width of said horizontal part;

two parts connected to said horizontal part and said front part at the sides to form blinders at the level of the temples of the wearer;

two notched parts each having a notch widened at the bottom and each being connected to each of a respective one of said sloping cutouts and being rectilinearly slidable in a lateral direction for rectilinar lateral slidability of the notches within said cutouts without producing a gap either at the top or sides of the notched parts, each of said notched parts defining an unobstructed field of view determined by the lateral position of the notch, for a fixed head position, and the distance of the notch from the eye, the greater the distance, the more limited the field of view;

pushbutton means connected to each of said notched parts for allowing easy lateral shifting adjustment thereof within said sloping cutouts; and marking means on each of said notched parts and on said front part for indicating the relative lateral position of each of said notched parts, wherein said support is pivotally connected to said adaptation means such that the support, and particularly said front part, may be tilted upwardly and downwardly, and wherein a portion of one side of each of said notched parts adjacent to and on the same side of each notch is made of tinted transparent material to absorb or reduce the intensity of light rays reaching the eye from certain angles outside the desired field of view.

2. A visor in accordance with claim 1 wherein said support is constructed of a flexible material, reinforced by an armature made of deformable metal wire, in order to allow said support, along with the reinforced armature, to be bent more or less inward to adapt to the shape of the wearer's face.

3. A visor in accordance with claim 2, wherein said adaptation means comprise an armature made of deformable metal wire connected to an eyeglass-type frame, said frame including a central nose piece intended to rest on the nose of the wearer.

4. A visor in accordance with claim 3, wherein the frame comprises two sides to rest on the ears, articulated on said blinder parts of said support, the central nose piece being attached to said horizontal part of said support.

5. A visor in accordance with claim 4, wherein said adaptation means comprise an elastic ribbon attached to the wearer's head.

6. A visor in accordance with claim 5, adaptable to a pair of corrective eyeglasses or sun glasses, worn by the wearer, wherein said adaptation means comprise a portion of metal wire insertable into holes made in the frame of said glasses or in tubes soldered thereto.

7. A visor in accordance with claim 6, adaptable to a motorcycle helmet, with or without a face shield, wherein said adaptation means comprise knurled screws and straps with clips.

8. A visor in accordance with claim 7, adaptable to a pair of corrective eyeglasses or sun glasses, worn by the wearer, wherein said adaptation means comprise the ends of said armature which are insertable into holes made in the frame of said glasses or in tubes soldered thereto.

* * * * *